US008026416B2

(12) United States Patent
van den Bosch et al.

(10) Patent No.: US 8,026,416 B2
(45) Date of Patent: Sep. 27, 2011

(54) BROCCOLI TYPE HAVING CURDS WITH DETACHED FLORETS

(75) Inventors: Franciscus van den Bosch, Kesteren (NL); Meinardus Petrus Boon, Scharwoude (NL)

(73) Assignee: Seminis Vegatable Seeds, Inc., St. Louis, MO (US)

( * ) Notice: Subject to any disclaimer, the term of this patent is extended or adjusted under 35 U.S.C. 154(b) by 1192 days.

(21) Appl. No.: 11/602,276

(22) Filed: Nov. 21, 2006

(65) Prior Publication Data

US 2007/0118935 A1    May 24, 2007

Related U.S. Application Data

(60) Provisional application No. 60/739,803, filed on Nov. 22, 2005.

(51) Int. Cl.
*A01H 5/00*    (2006.01)
(52) U.S. Cl. ...................................................... 800/306
(58) Field of Classification Search .................. None
See application file for complete search history.

(56) References Cited

U.S. PATENT DOCUMENTS

| 5,304,719 | A  | 4/1994  | Segebart |
| 5,367,109 | A  | 11/1994 | Segebart |
| 5,763,755 | A  | 6/1998  | Carlone |
| 5,850,009 | A  | 12/1998 | Kevern |
| 6,667,428 | B1 | 12/2003 | Chen et al. |
| 2004/0117877 | A1 | 6/2004 | Van den Bosch et al. |
| 2005/0262594 | A1 | 11/2005 | van den Bosch et al. |

FOREIGN PATENT DOCUMENTS

| WO | 02/085105 A2 | 10/2002 |
| WO | 03/090521 A2 | 11/2003 |
| WO | 2005/112610 A2 | 12/2005 |

OTHER PUBLICATIONS

Chen et al., "Transformation of broccoli (*Brassica oleracea* var. *italica*) with isopentenyltransferase gene via *Agrobacterium tumefaciens* for post-harvest yellowing retardation," *Molecular Breeding*, 7:243-257 (2001).
International Search Report issued in PCT/US2006/045008 on Aug. 10, 2009.
Page et al., "Molecular and Biochemical Characterization of Postharvest Senescence in Broccoli," *Plant Physiology*, 125:718-727 (2001).
Tan et al., "Storage characteristics and quality of four broccoli (*Brassica oleracea* var. *italica*) cultivars," *Australian Journal of Experimental Agriculture*, 33(1):111-113 (1993).
Tian et al., "A Role for Ethylene in the Yellowing of Broccoli after Harvest," *J. Amer. Soc. Hort. Sci.*, 119(2):276-281 (1994).
Tolvonen et al., "Differences in Cholorphyll Loss at 13°C. for Two Broccoli (*Brassica oleracea* L.) Cultivars Associated with Antioxidant Enzyme Activities," *J. Agric. Food Chem.*, 46:20-24 (1998).

Fujime, "Yasai Engei Dai-Hyakka," *Encyclopedia of Vegetable Gardening* 8:259-267 (1989) including an English language translation.
Registration of Plant Variety No. 3871 Japanese language (1994) including an English language translation.
Sakata Hybrid Shinkai, "Breeding Process, Sosai no Shin-Hinshu," *New Varieties of Vegetables* 9:127 (1985) including an English language translation.
Third Party Observation (Petition) from Japanese Patent Application No. 2008-542403(2010) including an English language translation.
Baggett et al., "Broccoli Breeding Lines OSU 101—OSU 115", *HortScience* 20(4):782-784 (1985).
Baggett et al., "Inheritance of Internode Length and its Relation to Head Exsertion and Head Size in Broccoli," *J. Amer. Soc. Hort. Sci.*, 120(2):292-296 (1995).
Bernacchi et al., "Advanced backcross QTL analysis in tomato. I. Identification of GQLs for traits of agronomic importance from *Lycoperiscon hirsutum*," *Theoretical and Applied Genetics*, 97(3):281-397 (1998).
Bernacchi et al., "Advanced backcross QTL analysis in tomato. II. Evaluation of near-isogenic lines carrying single-donor introgression for desirable wild QTL-alleles derived from *Lycoperiscon hirsutum* and *L. pimpinellifolium*," *Theoretical and Applied Genetics*, 97:170-180 (1998).
Bon, "Senior Design Project Development of a Non-Selective Broccoli Harvester," *American Society of Agricultural Engineers*, No. 97-1018, presentation at the 1997 International American Society of Agricultural Engineers Meeting, Minneapolis Convention Center, Minneapolis, Minnesota, Aug. 10-14, 1997, pp. 1-17.
Casada et al., "Single Pass Harvesting of Broccoli", *American Society of Agricultural Engineers*, Presentation at the 1988 International Summer Meeting of the ASAE, Rushmore Plaza Civic Center, Rapid City, South Dakota, Jun. 16-29, 1988.
Chen et al., "A Molecular Linkage Map of Tomato Based on a Cross Between *Lycopersicon esculentum* and *L. Pimpinellifolium* and its Comparison with Other Molecular Maps of Tomato," *Genome* 42:94-103 (1999).
Chetelat et al., "A male-fertile Lycopersicon esculentum X Solanum lycopersicoides hybrid enables direct backcrossing to tomato at the dipliod level," *Euphytica* 95:99-108 (1997).
Chetelat et al., "Tolerance to *Botrytis cinerea*," *Acta Horticulturae* 487:313-316 (1999).
Concibido et al., "Genome Mapping of Soybean Cyst Nematode Resistance Genes in 'Peking', PI 90763, and PI 88788 Using DNA Markers," *Crop. Sci* 37:258-264 (1997). Dellacecca "New Agrotechniques to Promote Broccoli Picking," *Proc. Int. Sym on Brassicas*, Ninth Crucifer Genetics Workshop, Ed. J.S. Dias, I. Crute, A.A. Monteiro Acta Hort. (ISHS) 407:347-352 (1996).
Doganlar et al., "Molecular Mapping of the py-1 gene for resistance to corky root rot (*Pyenochaeta lycopersici*) in tomato," *Theoretical and Applied Genetics*, 97:784-788 (1998).
Egashira et al., "Screening of Wild Accession Resistant to Gray Mold (*Botrytis cinerea* Pers.) in *Lycopersicon*," *Acta. Physiol. Plant*, 22(3):324-326 (2000).
Fulton et al., "Advanced backcross QTL analysis of a *Lycopersicon esculentum* X *Lycopersicon parviflorum* cross," *Theoretical and Applied Genetics*, 100(7):1025-1042 (2000).
Grube et al., "Comparative Genetics of Disease Resistance Within the Solanaceae," *Genetics*, 155:873-887 (2000).
Ignatova et al., "Resistance of Tomato F1 Hybrids to Grey Mold," *Acta Physiolo. Plant*, 22(3):326-328 (2000).

(Continued)

*Primary Examiner* — Elizabeth McElwain
(74) *Attorney, Agent, or Firm* — Alissa Eagle; Arnold & Porter LLP

(57) ABSTRACT

The present invention includes broccoli plants with curds having detached florets and methods for obtained such broccoli plants. The present invention also provides reagents that can be used in methods for obtaining such broccoli plants.

51 Claims, 6 Drawing Sheets
(3 of 6 Drawing Sheet(s) Filed in Color)

OTHER PUBLICATIONS

Kerr et al., "Resistance to Cladosporium Fulvum CKE. Obtained from Wild Species of Tomato", *Can. J. Botany* 42:1541-1558 (1964).

Klingler et al., "Mapping of Cotton-Melon Aphid Resistance in Melon," *J. Amer. Soc. Hort. Sci.*, 126(1):56-63 (2001).

Lee et al., "Identification of quantitative trait loci for plant height, lodging, and maturity in a soybean population segregating for growth habit," *Theor. Appl. Genet.*, 92:516-523 (1996).

Michelmore et al., "Identification of markers linked to disease-resistance genes by bulked segregant analysis: A rapid method to detect markers in specific genomic regions by using segregating populations", *Proc. Natl. Acad. Sci.*, 88:9828-9832 (1991).

Monforte et al., "Development of a set of near isogenic and backcross recombinant inbred lines containing most of the *Lycopersicon hirsutum* genome in a *L. esculentum* genetic background: A tool for gene mapping and gene discovery," *Genome* 43(5):803-813 (2000).

Moreau et al., "Genetic Mapping of Ph-2, a Single Locus Controlling Partial Resistance to *Phytophthora Infestans* in Tomato," MPMI 11(4):259-269 (1998).

Nelson, "QGENE: software for mark-based genomic analysis and breeding," *Molecular Breeding*, 3:239-245 (1997).

Poehlman et al., "Breeding Field Crops", 4$^{th}$ ed., Iowa State University Press, Ames, Iowa, p. 473 (1995).

Shear et al., "Multiple-Pass Selective Broccoli Harvester Field Trial," Presentation at the 1990 International Winter Meeting sponsored by the American Society of Agricultural Engineers, Hyatt regency Chicago, Chicago, Illinois, Dec. 18-21, 1990, Paper No. 901611.

Shearer et al., "A Cut-Off Saw Mechanism for Selective Harvest of Broccoli," *American Society of Agricultural Engineers*, 34(4):1623-1628 (1991).

Shearer et al., "Development of a Mechanized Selective Harvester for Cole Crops", *American Society of Agricultural Engineers*, presentation at the 1991 International Summer Meeting, Albuquerque Convention Center, Albuquerque, New Mexico, Jun. 23-26, 1991, Paper No. 911018.

Supplemental European Search Report dated Jul. 22, 2004 for EP Application No. 02 72 5774.

Tanksley et al., "High Density Molecular Linkage Maps of the Tomato and Potato Genomes," *Genetics*, 132:1141-1160 (1992).

Unilett Informations, "Chou Broccoli: LaRécolte Mécanique Devient Possible," 107:11-13 (2001) (in French with English translation).

Urbasch, "Resistance of Different Cultivated and Wild Tomato Plants Lycopersicon—SPP to Botrytis Cinerea", *Journal of Phytopathology*, 116(4):344-351 (1986) (abstract only in English).

van Ooijen et al., "An RFLP Linkage Map of *Lycopersicon Peruvianum*," *Theor. Appl. Genet.* 89:1007-1013 (1994).

Vidavsky et al., "Tomato breeding lines resistance and tolerant to tomato yellow leaf curl virus issued from *Lycopersicon hirsutum*," *Phytopathology*, 88(9):910-914 (1998).

Westman et al., "The potential for cross-taxa simple-sequence repeat (SSR) amplification between *Arabidopsis thaliana* L. and crop brassicas," *Theor, Appl. Genet.*, 96:272-281 (1998).

BROCCOLI TYPE HAVING CURDS WITH DETACHED FLORETS

CROSS-REFERENCE TO RELATED APPLICATIONS

This application claims priority under 35 U.S.C. §119(e) of provisional U.S. Application Ser. No. 60/739,803, filed Nov. 22, 2005.

BACKGROUND OF THE INVENTION

1. Field of the Invention

The present invention relates to the field of plant breeding and the development of new plants. More specifically, to the development of a new and distinct broccoli type (*Brassica oleracea* L. var. *italica*) having curds with detached florets that are uniformly green, i.e., show no yellowing or discoloration around the edges.

2. Background of the Invention

The botanical family to which broccoli belongs is the Brassicaceae (or referred to as Cruciferae), which is also known as the mustard family (or familiarly named as crucifers, as each flower has four distinct sepals and petals in the form of a cross). The Brassicaceae is a large family comprised of approximately 3,000 described species apportioned among 350 to 380 genera. The precise number of genera will vary depending on the authority. The classification scheme for broccoli and indeed for all of the other *brassica*'s is clear and straightforward until one reaches the species level. At that point the addition of numerous subspecies or cultivar groups results in a rather complex and confusing arrangement of the taxa in question. For example, the scientific name for broccoli, *Brassica oleracea* (L.), is also shared by cabbage, Chinese cabbage, cauliflower, collards, Brussels sprouts, kale, kohlrabi, to name a few. Despite the fact that all of the aforementioned types are sexually compatible, and are therefore referred to as *B. oleracea*, they are nevertheless separate entities.

The genus *Brassica* includes a number of notable vegetable crops other than *Brassica oleracea* (2n=18). The *Brassica* genus also includes vegetables or forage crops of many other genera. Most importantly in this context are *B. rapa* (2n=20) or turnip and *B. napus* (2n=38) or swede. At the species level taxonomic names used for broccoli are *Brassica oleracea* L. *convar botrytis* (L) *Alef.* var. *cymosa Duch*, *Brassica oleracea* L. *convar botrytis* (L) *Alef.* var. *italica Plenck* and *Brassica oleracea* L. var *italica Plenck*. Taxonomic experts have different opinions for reasons mentioned before. The Germplasm Resources Information Network (GRIN), of the United States Department of Agriculture, uses *Brassica oleracea* L. var *italica Plenck* in the GRIN Taxonomy for Plants to apply to broccoli. Broccoli is hereinafter referred to as *Brassica oleracea* L. var *italica*.

Broccoli is mostly consumed fresh. The part consumed is the fleshy-stemmed flowering head. Retailers sell such heads in its entirety. More recently, changes in fresh consumption have taken place in which the broccoli heads are separated into florets. The florets are packaged and sold as convenience foods, either solely as broccoli florets or as florets mixed with other fresh vegetables.

Many broccoli varieties grow best on well-drained soils that hold water. In sandy soils, irrigation is important for optimum plant growth and to maintain proper main curd. Curds develop relative to ambient temperatures, and in the heat of summer, broccoli curds maturing in July may produce flowers and seeds more quickly (four to six days) than those maturing in the cooler spring and fall periods.

To be considered good quality, broccoli curds should be closed, compact, dark green and tight (no yellow petals showing). A deep green, uniform curd color is a desirable trait in broccoli. Broccoli heads "green" according to the amount of sunshine reaching the crown of the curds, the crown being the upper surface of the broccoli curd covered by the florets. Current commercial 'heading broccoli' varieties all have a high leaf canopy that shades at least portions of the curd, particularly at the margin of the crown, resulting in yellowing around the outer extremities of the harvested broccoli curds, sometimes even causing extensive yellowing of individual florets at the center of the crown.

In a study reviewing harvest practices from 1995 to 1999 in the California, broccoli production costs broken down into 29 percent for land preparation, planting, and growing costs, 45 percent for harvest and post-harvest costs, 20 percent for cash overhead, 1 percent for interest on operating capital, and 5 percent for non-cash overhead costs. Hence, the labor requirements for harvesting are well over 50% of the total labor costs for growing broccoli. Since harvesting is the single most expensive cultural operation, it is imperative that these costs be kept to a minimum. One trend is to harvest only the main terminal curd, usually by hand. Certain mechanical harvest aids are used, but complete mechanical harvesting has not been adopted. Use of modern, more uniform hybrids has enabled growers to complete harvesting in two or, at the most, three manual cuts through the field.

Converting from hand to machine harvesting of broccoli could reduce these labor requirements by a great deal. However, in testing different cultivars, transplant times, growing techniques and harvest methods, a recent study determined that once over mechanical harvest of broccoli inflorescences, or curds, compared to the graduated traditional hand-harvest (picking repeatedly 6 to 8 times), results in a yield reduction on the order of 49% to 60%, depending on the variety. A combination of hand harvest for the primary curds, followed by a mechanical picking of the secondary curds was proposed as reducing yield losses, though still on the order of about 23%.

Another issue is the cost of processing broccoli after harvesting. Broccoli curds are often further processed into individual florets, mostly by hand, for freezing or to satisfy market demand for minimally processed fresh vegetable products. The amount of hand labor is very great to cut broccoli curds into separate florets, i.e., floretting. Before floretting of the main curd, it must often be first defoliated. In addition to requiring a great deal of hand labor, the florets separated individually from the curds are generally not very uniform in size and color, and often require additional trimming and processing before packaging. In the UK, the cost of harvesting broccoli in the field is about $50 per ton. The floretting cost per ton is approximately $120 to $140 ex field. The cost for floretting in a pack house is approximately $90 per ton.

Floretting broccoli curds for use as minimally processed food is generally done at the pack house away from the growing site for hygienic reasons. For this fresh market niche, floret size is preferred in the range of 20 to 80 mm, and with a trimmed square at the cut end. Broccoli is also increasingly being grown and floretted (florets cut from the head) for frozen products. For the frozen foods market, floret size is preferred in the range of 20 to 40 mm up to 40 to 65 mm, with the 20 to 40 mm being most valuable. Freezers prefer florets that are uniform in size and green color, as more attractive to the consumer.

Green florets are preferred, though a yellow halo is inevitable, given the growth habits of current varieties. About 10% pale yellow to dark cream is tolerated on the florets. All present commercial heading broccoli varieties have curds with very tightly packed florets. This results in individual florets, once separated from the curds, having the appearance of being partially yellow in color around the edges. Additionally, all present commercial broccoli varieties have curds that are placed deeply within the canopy. As a result of the shading and lack of uniform direct sunlight, curds, as well as the stalk, do no green uniformly, but show yellow discoloration, especially around the perimeter of the curd.

Therefore, there remains a need in the art for a broccoli plant type adapted for easier processing by producing a curd with florets uniformly green in color.

SUMMARY OF THE INVENTION

The present invention provides a seed of a broccoli plant capable of producing a plant comprising a curd having florets, where the florets on the curd have an average of less than 15% yellowing.

The present invention further provides a seed of a broccoli plant capable of producing a plant comprising a curd having detached florets, where at least 50% of said florets on the curd do not touch another floret on said curd.

The present invention also provides seed of a broccoli plant capable of producing a plant comprising a curd having florets, where the florets on the curd have an average length of at least about 10 centimeters.

The present invention also provides a container of broccoli seeds where curds grown from broccoli plants from greater than 50% of the seeds have detached florets.

Also provided are containers of broccoli seeds where curds grown from greater than 50% of the seeds have detached florets, wherein greater than 50% of the florets on the curd do not touch another floret on the same curd.

The present invention further provides a container of broccoli florets from a broccoli plant having a curd comprising detached florets, where the florets have an average of less than 15% yellowing.

The present invention also provides a broccoli plant having a curd with detached florets.

The present invention also provides a seed of a broccoli plant capable of producing a broccoli plant having a curd with detached florets.

Also provides are parts of a broccoli plant having a curd with detached florets, where the curd comprises at least 50% detached florets.

The present invention also provides a method of producing a broccoli seed comprising crossing a first parent broccoli line with a second broccoli line, wherein said first parent broccoli line comprises detached florets; and obtaining $F_1$ seed.

The present invention further provides a method of producing a broccoli plant having florets having an average yellowing of less than 15%, comprising crossing a first parent broccoli line with a second broccoli line, where the first parent broccoli line comprises curds having florets having an average of less than 15% yellowing; and obtaining $F_1$ seed.

The present invention also provides seed of broccoli line 550478, a sample of the seed having been deposited under NCIMB Accession No. 41416. The present invention also provides a seed of broccoli line 550479, a sample of the seed having been deposited under NCIMB Accession No. 41415. The present invention also provides a seed of broccoli line 550385, a sample of the seed having been deposited under NCIMB Accession No. 41417. The present invention also provides a seed of broccoli line 550198, a sample of the seed having been deposited under NCIMB Accession No. 41418.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
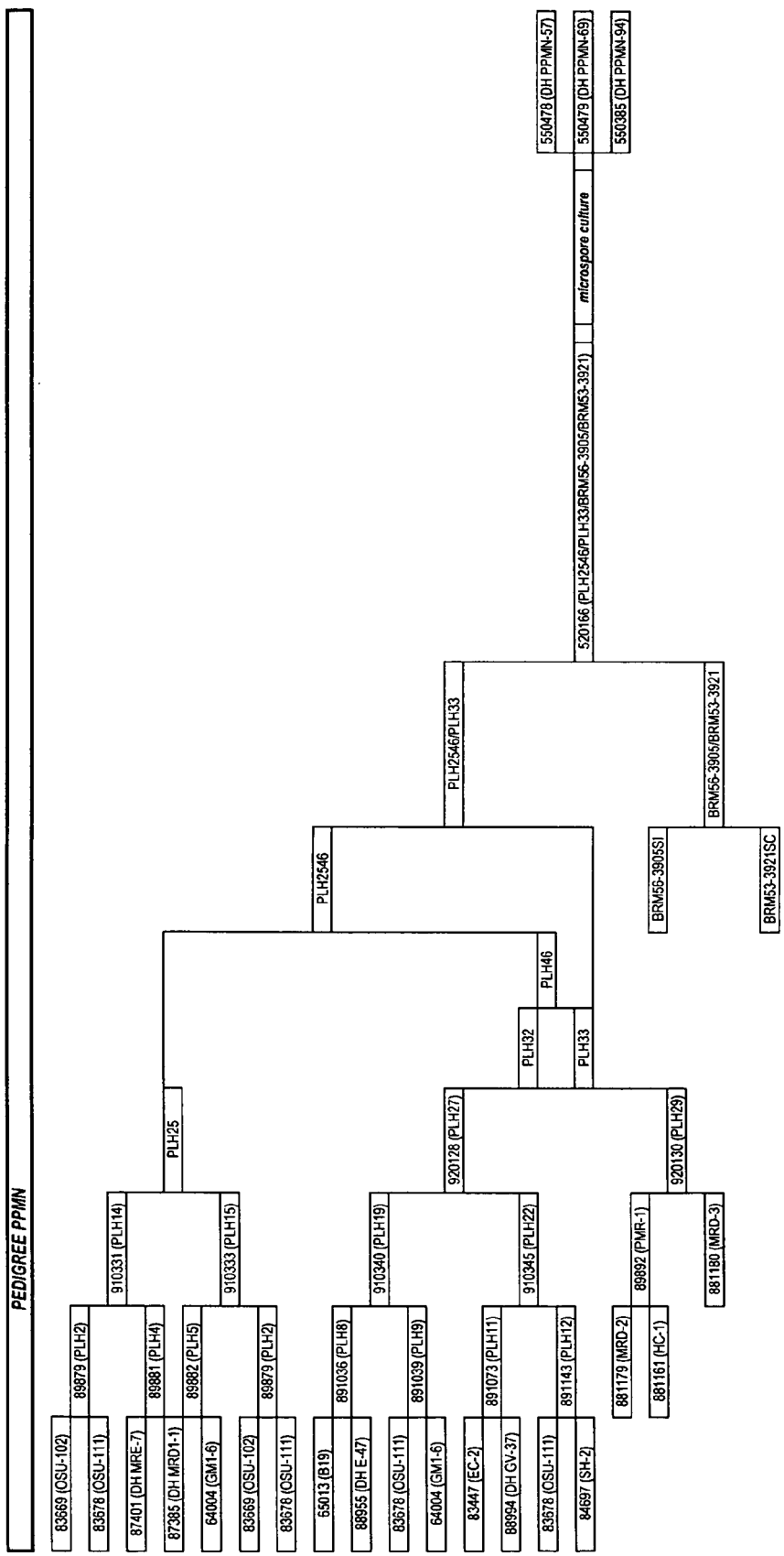
FIG. 1 is a chart showing the pedigree of the development of the detached floret lines 550478, 550479, and 550385.

The present invention provides a broccoli plant having a growth type comprising a main curd that has elongated secondary stems supporting detached florets. The present invention also provides a broccoli plant having a curd comprising detached florets that are uniformly green, and do not show substantial yellowing. In contrast, broccoli florets from current commercial heading broccoli cultivars are tightly packed into a curd and produce florets, especially interior florets that are substantially yellow.

DEFINITIONS

Technical or scientific terms used herein shall have the ordinary meaning accepted by those of skill in the art, unless defined differently herein. Descriptions of botanical terms can be found in numerous texts on the subject. See, for example, Hickey, M., and King, C., (2001). *Cambridge Illustrated Glossary of Botanical Terms*, Cambridge, UK: Cambridge University Press.

The term "broccoli plant" refers to broccoli plants of species *Brassica oleracea* L. var *italica* embracing broccoli varieties, breeding lines, inbred lines, hybrids, and the like.

A "variety" or "cultivar" is used herein in conformity with the International Union for the Protection of New Varieties of Plants ("UPOV") convention and refers to a plant grouping within a single botanical taxon of the lowest known rank, which grouping can be defined by the expression of the characteristics resulting from a given genotype or combination of genotypes, can be distinguished from any other plant grouping by the expression of at least one of the said characteristics and is considered as a unit with regard to its suitability for being propagated unchanged (stable).

The term "commercial broccoli cultivar" or, "commercial heading broccoli", as used herein, refers to currently available broccoli cultivars (or varieties), such as Marathon, Decathlon, Triathlon, Heritage, Legacy and Ironman. Such varieties are also referred to as "traditional" varieties.

"Growth type" or "type" refers to one or more morphological (phenotypic) features of a plant, such as overall plant height, leaf presence/absence, leaf size and position, curd height, curd structure, curd size/weight, length of branching, etc.

"Secondary stem" as that term is used herein, means a stalk that branches from the main stalk of the broccoli plant above the point of severing the harvested head and supporting and forming part of individual florets.

As used herein, a "floret" refers to the flower bud cluster including that part of the secondary stem supporting the flower bud cluster, which collectively make up the curd. The secondary stem branches from the main stem, and divides further into tertiary, quarternary, etc. stems until at the end a single filament supports an individual flower bud. The floret provides a dense cluster of unopened broccoli flower buds, with the floret having a diameter of 40 to 80 mm, preferably having a diameter of 40 to 60 mm. These unopened flower buds are also referred to herein as "beads."

The term "curd," as used herein, refers to a collection of florets in a single floral structure. These florets traditionally form a solid curd. The term "main curd" refers to the curd that forms at the terminus of the main stem and excludes secondary curds from side shoots, which originate from the axillary buds of the leaves. The term "head" is also used to refer to this floral structure.

The term "semi-detached floret" refers to traditional broccoli plants showing some intermediate exsertion of the curd. For broccoli having semi-detached florets, the individual florets are not standing alone, but remain close and touching each other. Some exserted head broccoli has the trait of semi-detached florets, for instance SVR 5 is an example of a semi-detached floret type. For such lines, the secondary stem is shorter than is the case for detached floret broccoli. SVR 5 was produced by crossing PLH2546/PLH33 with BRM53-3921SC, a proprietary Seminis line. Line PLH2546/PLH33, was also used in the development of the lines of the present application.

The term "detached florets" refers to a plant growth type with a curd in which the secondary stems or stalks are longer than the secondary stalks of commercial broccoli cultivars, on the order of a minimum of 5 centimeters in total length measured from the point of branching from the main stalk to the tip of the floret. Detached florets also grow in such a way as to permit a 5-6 cm (diameter) floret to stand alone in the curd and be separated from the neighbor florets (no touching or at most de minimis touching of less than a few radians of the floret circumference). In one aspect, detached florets have less than 10, 9, 8, 7, 6, 5, 4, 3, 2, 1 flower buds in contact with a flower bud of another floret. In a preferred aspect, a detached floret has no flower buds in contact with a flower bud on another floret. Preferred florets have a length of 5 to 8 cm. In another aspect, florets have a length of at least 8, 9, 10, 11, 12, 13, 14, 15, 16, 17, 18, 19, 20, 21, 22, 23, 24, 25, 26, 27, 28, 29, 30 cm. The detached florets grow together from a primary stalk, forming a more open curd than traditional broccoli, which permits easier processing of the florets at harvest for fresh market or freezing, either by hand or by mechanized means. In one aspect, at least 50%, 60%, 70%, 80%, 90%, 95%, 96%, 97%, 98%, 99% of the florets on a curd do not contact another floret on the same curd.

"Yellowing" or "discoloration" refers to the presence of yellow flower buds in the florets (e.g., generally at the margins) as a result of shading. A floret having "substantially no yellowing" refers to a floret having less than 15% yellowing as measured by the percentage of coverage across the floret having a yellow appearance. A floret having an "absence of yellowing" refers to a floret having less than about 5% yellowing as measured by the percentage of coverage across the floret having a more yellow than green appearance. In another aspect, florets on a curd have an average of less than 15%, 14%, 13%, 12%, 11%, 10%, 7.5%, 5% yellowing as measured by the percentage of coverage across the floret having a more yellow than green appearance. Yellowing can be measured at any time during the development of the florets, at harvest, or post harvest after a period of storage. In a preferred aspect, the yellowing is measured at maturity of the floret at harvest, as measured by the percentage of coverage across the floret having a more yellow than green appearance. In a preferred aspect, yellowing is measured as an average yellowing of a population of florets from a curd. In a preferred aspect, a broccoli plant of the present invention comprises a curd having an average yellowing of less than about 15%, 14%, 13%, 12%, 11%, 10%, 9%, 8%, 7%, 6%, 5% as measured by the percentage of coverage across the florets having a more yellow than green appearance.

The term "uniformly green" refers to a curd or a floret having substantially no yellowing. A uniform green floret is substantially green. This color attribute extends to the entire floret, including the part of the secondary stem supporting the flower bud cluster. Color classifications used to describe the florets are based on the color chart of the Royal Horticultural Society (RHS Color Chart), which is the standard reference for flower colors and used by specialists organizations such as the International Union for the Protection of New Varieties of Plants (UPOV). Florets of the plants of the invention are classified in the "green group" and are uniform for the color (for example 137A/B, 138A/B). Florets of traditional broccoli varieties have substantial portions, an average of at least 15% of the individual florets on a curd, which are classified in the "yellow-green" group (for example 144B/C, 149D-150D, and 154B/C/D). Individual florets on traditional broccoli varieties may have as low as 10% yellowing. This color difference is based on the color of the florets (including stems) when viewed from the side after separation from the curd. The stem of the florets of traditional broccoli varieties also classify in the "yellow-green" group (144 B/C and 145 B/C/D) while the stems of the florets of the present invention classify in the "green" group (137A/B, 138A/B/C, and 139D) This description is in accordance with UPOV terminology and the color terminology herein is in accordance with The Royal Horticultural Society Colour Chart (R.H.S.C.C.) and the color descriptions refer to plate numbers in the aforementioned color chart. Color designations, color descriptions and other phenotypic descriptions may deviate from the stated values and descriptions depending upon variation in environmental, seasonal, climatic and cultural conditions. Where a color reference is given these refer to the RHS Colour Chart, The Royal Horticultural Society, London. 2001 Edition.

"Uniformity" refers to a field of plants being uniform in their phenotypic appearance and development, especially with respect to plant maturity, curd height and structure, leafless stalk, absence of yellowing, etc. The harvested plants will, therefore, also be uniform in maturity, appearance, shelf-life, firmness, etc. Obviously, uniformity does not exclude some degree of plant to plant variation, but variation of a uniform crop is minimal. Depending on the trait measured, mean plant to plant variation of a field is preferably less than 10%, 9%, 8%, 7%, 6%, 5%, 4%, 3%, 2%, more preferably less than 1%. Further, the mechanical harvesting will enable a uniform (pre-determined) stalk length to be present in the harvested curd.

"Shelf-life" refers to the time period after harvest during which the plants (the curd and/or the stalk) can be stored without quality loss, such as discoloration and loss of firmness. The shelf-life depends on the genetic make-up of the plant and storage conditions such as temperature, relative humidity, light, etc. In a preferred aspect, at zero degrees Celsius and 95-100% relative humidity the shelf-life is preferably at least 7, 8, 9, 10, 11, 12, 13, 14, 15, 16, 17, 18, 19, 20 days, or more.

A "harvested plant" or "harvested broccoli" or "harvested head" refers to the severed curd, comprising part of or the entire main or primary stalk. Preferably, the harvester can be set to cut a specific height (cm distance) above ground, so that the length of the leafless stalk attached to the harvested head can be predetermined and is uniform for the harvested crop (the leafless stalk present may for example be 5, 10, 15, 20, 25 cm long or more).

Reference to an element by the indefinite article "a" or "an" does not exclude the possibility that more than one of the element is present, unless the context clearly requires that there be one and only one of the elements. The indefinite article "a" or "an" thus usually means "at least one."

The term "comprising" is to be interpreted as specifying the presence of the stated parts, steps or components, but does not exclude the presence of one or more additional parts, steps or components. A plant comprising a certain trait may thus comprise additional traits.

Whenever reference to plants according to the invention is made, it is understood that also plant parts (cells, tissues, seeds, severed parts such as curds and/or stalks) are encompassed therein. Also encompassed are progeny of the plants which retain the distinguishing characteristics of the parents (especially the uniform green floret color and/or detached floret traits), such as seed obtained by selfing or crossing, e.g. hybrid seed, obtained by crossing two inbred parental lines, hybrid plants and plant parts derived therefrom, unless otherwise indicated.

Traits of Broccoli with Detached Florets

Current commercial heading broccoli has a thick main stem that branches into, sturdy secondary stems with an average length of 5 to 6 centimeters each supporting a floret.

In one aspect, the present application provides broccoli plants having detached florets. In one aspect, the broccoli plants have detached florets, such that the slender, sturdy secondary stems each supporting and being part of a floret are substantially longer, or extended, than secondary stems of current commercial heading broccoli. In one aspect, the secondary stems are about 7, 8, 9, 10 or more centimeters long. In another aspect, a curd has detached florets having an average length of the secondary stem of about 7, 8, 9, 10, or more centimeters.

In another aspect, the broccoli plants of the present invention have curds comprising at least six detached florets, and, more preferably, 7, 8, 9, 10, 11, 12, 13, 14, 15, 16, 17, 18, or more florets. In one aspect, the secondary stems support detached florets that form a main head or curd.

In another aspect, the present invention provides a broccoli plant having a curd in which at least 50%, 55%, 60%, 65%, 70%, 75%, 80%, 85%, 90%, 95%, 98% or greater of the florets are not touching any other floret on the curd. In another aspect, a broccoli plant has a curd having florets which have about, or at least about, 1, 2, 3, 4, 5, 6, 7, 8, 9, 10 or more millimeters between the florets.

The present invention also provides broccoli plants having a curd of a uniform green color, ranging from deep green to light green (RHS Color Chart "green group"). In one aspect, the broccoli plants have substantially no yellowing, preferably the broccoli plants have a curd having an absence of yellowing. While not intending to be limited to any particular theory, the detached florets develop a uniform green color as sunlight access and penetration is facilitated by the detached floret growth habit. In one aspect, substantially no yellowing is seen on the detached florets because the florets each stand separately from the next and are exposed to full sunlight across the floret surface. Stems and parts of the florets of traditional broccoli varieties are yellow-green according to the RHS Color Chart.

In another aspect, the broccoli plants of this invention have a curd with detached florets having a secondary stem length of at least 7, 8, 9, 10, 11, 12, 13, 14, 15, 16, 17, 18, 19, 20 cm. In one aspect, a broccoli plant has detached florets having a secondary stem length between about 7 cm and about 30 cm, between about 7 cm and about 27.5 cm, between about 8 cm and about 30 cm, and between about 9 cm and about 25 cm. In a preferred aspect, the length of the secondary stem is measured from the tip of the floret to the base of the secondary stem at the point of attachment to the primary stem. In another aspect, the broccoli plants of the present invention have detached florets having a diameters of about, or at least about 3, 4, 5, 6, 7, 8, 9 cm. In another aspect, the detached florets of the broccoli plants of the present invention are between 4 and 10 cm, preferably between 4 and 9 cm, or 4 and 8 cm and most preferably between 4 and 6 centimeters in diameter. In one aspect, a narrower diameter range may be preferred among a population of florets for uniformity in packaging. Diameter can be measured as a cross section measurement taken through the flower bud structure at the widest point.

In one aspect of the present invention, detached florets are more easily severed from the curds than is the case for traditional curds of the current compact heading commercial broccoli varieties.

In another aspect, the detached florets are also firm and compact, consisting of closely packed beads or flower buds typical of heading broccoli. In a preferred aspect, the detached florets of the present invention do not have the loose bead cluster growth type typical of broccolini or broccoli raab. The firmness of broccoli florets can be determined through visual inspection or by measuring the number of beads per square centimeter of floret surface.

The broccoli plants of the present invention preferably have firm florets. In one aspect, a firm, or tightly packed, floret has about, or at least about, 25, 26, 27, 28, 29, 30, 31, 32, 33, 34, 35, 36, 37, 38, 39, 40, 41, 42, 43, 44, 45, 46, 47, 48, 49, or 50 flower buds per square cm. In one aspect, individual flower buds (beads) range in size between 1.50 and 2.25 mm. In one aspect, the buds are not all in one plane or sphere, but at different heights, and are not uniform in size, with buds in the middle, younger florets being smaller than the outer ones. In one aspect, florets in the apex of the curd of the plant are more tightly arranged, and a few may lack the fully detached character.

In one aspect, the broccoli plants of the present invention have florets that have a weight of about, or at least about, 2, 3, 4, 5, 6, 7, 8, 9, 10, 11, 12, 13, 14, 15, 16, 17, 18, 19, 20, 21, 22, 23, 24, 25 grams. Weight of the floret can be measured using any method available. In a preferred aspect, the weight of the floret is measured by weighing the floret cut to the length equal to the diameter of the floret (the "weight of the square floret"). In one aspect, the florets from a broccoli curd have an average weight of about 10, 11, 12, 13, 14, 15, 16, 17, 18, 19, 20, 21, 22, 23, 24, or 25 grams.

In one preferred aspect, at least 50%, 55%, 60%, 65%, 70%, 75%, 80%, 85%, 90%, 95%, 96%, 97%, 98%, 99% of the florets on a broccoli curd do not contact another floret on the same broccoli curd. In a preferred aspect, none of the florets on a broccoli curd contact another floret. In one aspect, the broccoli plants of the present invention have curds that allow for ease of harvest of the broccoli curds and separation of the florets from the curd. In another aspect, the broccoli curds of the present invention have detached florets which allow for increased exposure to sunlight for each of the florets on the curd. In one aspect, the detached florets receive 80%, 85%, 90%, 95%, 96%, 97%, 98%, 99% sunlight over the surface area of each floret on the broccoli curd. In one aspect, where the florets are not touching, uniform coloring by sunlight results.

In another aspect of the present invention the curd of the broccoli plant of the invention is also exserted above the leaf canopy. In one aspect, the curd exsertion contributes to even greater sunlight exposure to the detached florets.

As used herein, "raised head" or "exserted head" refers to a plant growth type, wherein the curd develops above the leaf canopy of the plant. In one aspect, the crown of the curd is raised by at least about 2, 3, 4, 5, 6, 7, 8, 9, 10, 11, 12, 13, 14, 15, 16, 17, 18, 19, 20, 21, 22, 23, 24, 25 or more centimeters above the leaf canopy. The "crown" refers to the uppermost part of the curd, i.e., top of the curd covered by the packed inflorescences. "Below the head" refers to the area below the curd, i.e., below the attachment of the substantial portion of the florets to the stem and above the point of severing the head at harvest. Such broccoli plants are described in the U.S. patent application Ser. No. 10/850,077 entitled "Broccoli Type Adapted For Ease of Harvest", Publication No. 20050262594, the contents of which are incorporated in their entirety by reference.

Exserted curds are at least 10, 11, 12, 13, 14, 15, 16, 17, 18, 19, 20, 21, 22, 23, 24 centimeters higher than the top of the canopy, and in preferred embodiments at least 25 centimeters higher than the top of the canopy. In addition, exserted broccoli plant types may have a substantial absence of leaves and leaflets along the stalk immediately below the curd. This also allows for easier harvesting, as curds do not require defoliation after harvesting. In one embodiment, within 25 centimeters below the crown of the curd, the plant produces substantially no leaves or petioles having a surface area greater than about 30 square centimeters, preferably greater than about 20 square centimeters. In a particularly preferred embodiment, substantially no leaves or petioles are produced within 25 centimeters below the crown.

The present invention also provides a seed of a broccoli plant capable of producing a broccoli plant in which curds obtained from broccoli plants grown for the seed have detached florets.

In another aspect, the present invention also provides for a plant grown from the seed of a broccoli plant in which curds obtained from broccoli plants grown for the seed have a detached floret trait, as well as plant parts and tissue cultures from such plants.

The present invention also provides a container of broccoli seeds in which curds obtained from broccoli plants grown from greater than 50% of the seeds have a detached floret trait. In another aspect, curds obtained from broccoli plants grown from greater than 55%, 60%, 65%, 70%, 75%, 80%, 85%, 90%, 95% of the broccoli seeds in the container have a detached floret trait.

The container of broccoli seeds may contain any number, weight or volume of seeds. For example, a container can contain at least, or greater than, about 10, 25, 50, 75, 100, 200, 300, 400, 500, 600, 700, 800, 900, 1000, 1500, 2000, 2500, 3000, 3500, 4000, 4500, 5000 or more seeds. Alternatively, the container can contain at least, or greater than, about 1 ounce, 5 ounces, 10, ounces, 1 pound, 2 pounds, 3 pounds, 4 pounds, 5 pounds or more seeds.

Containers of broccoli seeds may be any container available in the art. By way of non-limiting example, a container may be a box, a bag, a packet, a pouch, a tape roll, a pail, a foil, or a tube.

In another aspect, the seeds contained in the containers of broccoli seeds can be treated or untreated broccoli seeds. In one aspect, the seeds can be treated to improve germination, for example, by priming the seeds, or by disinfection to protect against seed-born pathogens. In another aspect, seeds can be coated with any available coating to improve, for example, plantability, seed emergence, and protection against seed-born pathogens. Seed coating can be any form of seed coating including, but not limited to pelleting, film coating, and encrustments.

In another aspect, the present invention also provides a container of broccoli florets in which greater than 50% of the florets are obtained from a broccoli plant having detached florets. In another aspect, greater than 55%, 60%, 65%, 70%, 75%, 80%, 85%, 90%, 95% of the florets in the container are obtained from a broccoli plant having detached florets.

In another aspect, the present invention provides a container of broccoli florets in which greater than 50% of the florets have substantially no yellowing. In a preferred aspect, greater than 55%, 60%, 65%, 70%, 75%, 80%, 85%, 90%, or 95% of the florets have substantially no yellowing. In another aspect, greater than 50%, 55%, 60%, 65%, 70%, 75%, 80%, 85%, 90%, or 95% of the florets in the container have an absence of yellowing.

The container of florets may contain any number, weight or volume of florets. For example, a container can contain at least, or greater than, about 5, 10, 15, 20, 25, 30, 35, 40, 45, 50, or 100 florets. Alternatively, the container can contain at least, or greater than, about 1 pound, 2 pounds, 3 pounds, 4 pounds, 5 pounds or more florets.

Containers of florets may be any container available in the art. By way of non-limiting example, a container may be a box, a flat, a clamshell, a bag, a packet, or a bunch. A container of florets of the present invention may be found in any location, including, but not limited to a warehouse, a distributor, a wholesaler, or a retail market, such as a grocery store.

Breeding and Development of Inbreds and Hybrids with the Detached Floret Growth Type Any broccoli plant having a suitable floret type can be used in conjunction with the present invention. Broccoli plants with suitable floret type can be used in the methods of the present invention. In a preferred aspect, the source of a detached floret type is an inbred broccoli plant. In an aspect, suitable detached floret broccoli plants may be produced by breeding with the following sources: DH MRE-7, DH MRD1-1, GM-1.6, B19, DH E-47, EC-2, DH GV-37, SH-2, OSU-102, OSU-111, MRD-2, HC-1, BRM56-3905, BRM53-3921, DC3EC6, 1032-1104 and 2151xT&A. In one aspect, a detached floret source broccoli plant can be identified by determining the floret type of a source broccoli plant, for example as semi-detached floret type or an exserted head type. In another aspect, a detached floret source broccoli plant may be crossed with any inbred or elite broccoli line having desired properties.

In one aspect, a detached floret-plant type can be identified in the progeny of certain crosses after microspore culture. Microspore culture can be used in exploiting recessive characteristics, and can also provide a method of producing genetically stable homozygous lines when fixed by chromosome doubling. Microspore culture is a breeding tool that is well known in the art, for example in U.S. Pat. No. 6,200,808, the entirety of which is incorporated herein by reference. In one aspect, continuous selection for raised head broccoli plant types can be used to obtain broccoli plant types with curds of a variable structure. In one aspect, such methods produce erect and tall plant types, supporting a compact curd with densely packed compact florets. Such methods can also produce shorter and less erect plant types, but with the secondary branches of the florets extending from the main stem under a larger angle (more horizontal). However, because of the shortness of the secondary stems, the florets touch each other. Such growth types can be classified as plants having a semi-detached curd. In one aspect, the broccoli plants of the present invention can be produced using crosses between the semi-detached broccoli plants and erect plants with an exserted curd, in combination with microspore culture.

The broccoli plants of the present invention can be homozygous or heterozygous. Plants that have been self or sib-pollinated once or twice followed by self or sib pollination and selected for type over many generations may retain some genotypic heterozygosity, but become phenotypically uniform. A cross between two such heterozygous but homogeneous parents produces a phenotypically uniform population of hybrid plants that are heterozygous for many gene loci. The development of such parent lines generally requires at least about 5 to 7 generations of selfing and/or sib mating. Two such parent lines can then be crossed to develop improved $F_1$ hybrids. Hybrids can then be screened and evaluated in small scale field trials. Typically, about 10 to 15 phenotypic traits, selected for their potential commercial value, can be measured. In another aspect, dihaploid plants are developed and these plants are genotypically uniform. Two such plants can be crossed, or a conventionally produced parent line described above can be crossed with a dihaploid, producing $F_1$ hybrids that are evaluated as described above.

The present invention also provides progeny of broccoli plants having detached florets. As used herein, the progeny include not only, without limitation, the products of any cross (be it a backcross or otherwise) between two plants, but all progeny whose pedigree traces back to the original cross. Specifically, without limitation, such progeny include plants that have 50%, 25%, 12.5% or less genetic material derived from one of the two originally crossed plants. As used herein, a second plant is derived from a first plant if the second plant's pedigree includes the first plant.

Broccoli plants generated using a method of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches, for breeding the plants of the present invention are set forth below. A breeding program can be enhanced using any method available, such as, marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, seed set, seed density, curd size, exsertion etc. will generally dictate the choice.

The present invention provides processes of preparing novel broccoli plants and broccoli plants produced by such processes. In accordance with such a process, a first parent broccoli plant may be crossed with a second parent broccoli plant wherein at least one of the first and second broccoli plants is a parent line or dihaploid line or detached floret broccoli plant as described herein. One application of the process is in the production of $F_1$ hybrid plants. Another important aspect of this process is that the process can be used for the development of novel parent, dihaploid or inbred lines. For example, a detached floret broccoli plant as described herein could be crossed to any second plant, and the resulting hybrid progeny each selfed and/or sibbed for about 5 to 7 or more generations, thereby providing a large number of distinct, parent lines. These parent lines could then be crossed with other lines and the resulting hybrid progeny analyzed for beneficial characteristics. In this way, novel lines conferring desirable characteristics could be identified.

Broccoli plants (*Brassica oleracea* L. var. *italica*) can be crossed by either natural or mechanical techniques. Mechanical pollination can be effected either by controlling the types of pollen that can be transferred onto the stigma or by pollinating by hand.

In another aspect, the present invention provides a method of producing a broccoli plant having detached florets comprising: (a) crossing a first broccoli line with a second broccoli line to form a segregating population, where the first broccoli line has detached or semi-detached florets; (b) screening the population for detached florets; and (c) selecting one or more members of the population having detached florets.

In another aspect, the present invention provides a method of introgressing a detached floret trait into a broccoli plant comprising: (a) crossing at least a first broccoli line having detached or semi-detached florets with a second broccoli line to form a segregating population; (b) screening the population for detached florets; and (c) selecting at least one member of the population having detached florets.

Parental plants are typically planted in pollinating proximity to each other by planting the parental plants in alternating rows, in blocks or in any other convenient planting pattern. Where the parental plants differ in timing of sexual maturity, it may be desired to plant the slower maturing plant first, thereby ensuring the availability of pollen from the male parent during the time at which the stigmas on the female parent are receptive to pollen. Plants of both parental parents are cultivated and allowed to grow until the time of flowering. Advantageously, during this growth stage, plants are in general treated with fertilizer and/or other agricultural chemicals as considered appropriate by the grower.

Alternatively, in another aspect of the invention, both first and second parent broccoli plants can be a detached floret broccoli plant as described herein. Thus, any broccoli plant produced using a detached floret broccoli plant as described herein forms a part of the invention. As used herein, crossing can mean selfing, sibbing, backcrossing, crossing to another or the same parent line, crossing to populations, and the like. All broccoli plants produced using a detached floret broccoli plant as described herein as a parent are, therefore, within the scope of this invention.

In another aspect, the present invention provides a hybrid broccoli plant having detached florets. In another aspect, the present invention provides seed of a hybrid broccoli plant having detached florets. Any time a detached floret broccoli plant as described herein is crossed with another, different, broccoli parent line, a first generation ($F_1$) broccoli hybrid plant is produced. As such, an $F_1$ hybrid broccoli plant can be produced by crossing a detached floret broccoli plant, for example, as described herein with any second parent broccoli plant. Essentially any other broccoli plant can be used to produce a hybrid broccoli plant having a detached floret broccoli plant as described herein as one parent. All that is required is that, at a minimum, one plant be female fertile and the second plant be male fertile.

A single cross hybrid broccoli variety is the cross of two parent lines, each of which has a genotype which complements the genotype of the other. Typically, $F_1$ hybrids are more vigorous than their parents. This hybrid vigor, or heterosis, is manifested in many polygenic traits, including improved yields, better roots, better uniformity and better insect and disease resistance. In the development of hybrids only the $F_1$ hybrid plants are typically sought. An $F_1$ single cross hybrid is produced when two parent plants are crossed. A double cross hybrid is produced from four parent plants crossed in pairs (A×B and C×D) and then the two $F_1$ hybrids are crossed again (A×B)×(C×D). A three-way cross is produced from three parent plants crossed as (A×B)×C.

In one aspect, any of the broccoli varieties known to those of skill in the art can be crossed with a detached floret broccoli line of the present invention to produce a hybrid plant. In a preferred aspect, such broccoli varieties include, but are not limited to Marathon, Decathalon, Heritage, Legacy, and Ironman.

When a detached floret broccoli plant as described herein is crossed with another parent plant to yield a hybrid, it can serve as either the maternal or paternal plant. For many crosses, the outcome is the same regardless of the assigned sex of the parental plants. Depending on the seed production characteristics relative to a second parent in a hybrid cross, it may be desired to use one of the parental plants as the male or female parent. Therefore, a decision to use one parent plant as a male or female may be made based on any such characteristics as is well known to those of skill in the art.

The development of new varieties using one or more starting varieties is well known in the art. In accordance with the invention, novel varieties may be created by crossing a detached floret broccoli plant as described herein followed by multiple generations of breeding according to such well known methods. New varieties may be created by crossing a detached floret broccoli plant as described herein with any second plant. In selecting such a second plant to cross for the purpose of developing novel parent lines, it may be desired to choose those plants which either themselves exhibit one or more selected desirable characteristics or which exhibit the desired characteristic(s) when in hybrid combination. Examples of potentially desired characteristics include greater yield, resistance to insecticides, herbicides, pests, and disease, tolerance to heat and drought, reduced time to crop maturity, better agronomic quality, higher nutritional value, and uniformity in germination times, growth rate, maturity, and root size.

Once initial crosses have been made with a detached floret broccoli line of the present invention, selfing and/or sibbing take place to produce new parent lines. The development of parent lines requires manipulation by human breeders. A combination of self pollination and sib pollination is essential to develop a new parent line that is genotypically stable and phenotypically uniform. The reason for the breeder to create parent lines is to develop homogeneous populations in an outcrossing species that are phenotypically uniform and can be utilized to produce $F_1$ hybrids.

The pedigree breeding method involves crossing two genotypes. Each genotype can have one or more desirable characteristics lacking in the other; or, each genotype can complement the other. If the two original parental genotypes do not provide all of the desired characteristics, other genotypes can be included in the breeding population. Superior plants that are the products of these crosses are selfed or sibbed and selected in successive generations. Each succeeding generation becomes more genetically homogeneous and phenotypically uniform as a result of self- or sib-pollination and selection. Typically, this method of breeding involves five or more generations of selfing or sibbing and selection. After at least five generations, the resulting parent line has a stable allelic frequency at each locus and is phenotypically uniform.

Many traits have been identified that are not regularly selected for in the development of a new variety but that can be improved by backcrossing techniques. A genetic locus conferring the traits may or may not be transgenic. Examples of such traits known to those of skill in the art include, but are not limited to, male sterility, herbicide resistance, resistance for bacterial, fungal, or viral disease, insect resistance, male fertility and enhanced nutritional quality. These genes are generally inherited through the nucleus, but may be inherited through the cytoplasm. Some known exceptions to this are genes for male sterility, some of which are inherited cytoplasmically, but still act as a single locus trait.

Direct selection may be applied where a genetic locus acts as a dominant trait. An example of a dominant trait is the herbicide resistance trait. For this selection process, the progeny of the initial cross are sprayed with the herbicide prior to the backcrossing. The spraying eliminates any plants which do not have the desired herbicide resistance characteristic, and only those plants which have the herbicide resistance gene are used in the subsequent backcross. This process is then repeated for all additional backcross generations.

Many useful traits are those which are introduced by genetic transformation techniques. Methods for the genetic transformation of broccoli are known to those of skill in the art. For example, methods which have been described for the genetic transformation of broccoli may include electroporation, electrotransformation, microprojectile bombardment, *Agrobacterium*-mediated transformation, direct DNA uptake transformation of protoplasts and silicon carbide fiber-mediated transformation. See, e.g., Khachatourians, G., et al., eds., Transgenic Plants and Crops, Marcel Dekker, Inc. (2002) and Fruit and Vegetable Biotechnology (Victoriano Valpuesta ed. Woodhead Publ. 2002).

It is understood to those of skill in the art that a transgene need not be directly transformed into a plant, as techniques for the production of stably transformed broccoli plants that pass single loci to progeny by Mendelian inheritance is well known in the art. Such loci may therefore be passed from parent plant to progeny plants by standard plant breeding techniques that are well known in the art. Examples of traits that may be introduced into a broccoli plant according to the invention include, for example, male sterility, herbicide resistance, disease resistance, insect resistance, and enhanced nutritional quality.

PCR and Southern hybridization are two examples of molecular techniques that can be used for confirmation of the presence of a given locus and thus conversion of that locus.

The detached floret trait can be any genotype, including but not limited to dominant, recessive, or a quantitative trait. In a preferred aspect, the inheritance of the detached floret broccoli trait recessive. In one aspect, the detached floret broccoli type is homozygous or heterozygous. In one aspect, microspore culture can be used to develop a homozygous breeding line. Inbred lines are also important for the development of detached floret hybrid plants, where both parents need to have the detached floret trait.

Broccoli plants of the detached floret growth type, deposited with the ATCC as described below, or derivatives there from which retain the growth types of these plants, can be used as parental lines. The detached floret trait may be transferred to other broccoli plants by using conventional breeding techniques and selecting progeny that retain the growth type of the parents, i.e. having secondary stems supporting detached florets with no substantial yellowing around their margins.

Also provided is a method of producing hybrid broccoli plants which have detached florets. This method involves crossing two (preferably di-haploid) plants according to the invention and harvesting the hybrid seeds. The seeds obtained will, when grown, show the novel growth type, in particular the extended and separated secondary stem stalk and detached florets, as defined. In one embodiment the method comprises the steps of planting rows of male and female parents of inbred plants according to the invention in a field, growing the plants until flowering and seed set has occurred, and harvesting the hybrid seed from the row of female parents. The method preferably prevents any self-pollination of the female parents from occurring in order to obtain 100% pure hybrid seeds (see below).

Seed Production

For large scale hybrid seed production, different systems of cross pollination, based on self-incompatibility, or, alternatively, cytoplasmic male sterility (CMS), can be used. These techniques are well known in the art. Large scale increase of the hybrid parents (inbred lines) is done by self-pollination, where necessary facilitated by increasing the concentration of $CO_2$ to overcome the self-incompatibility, or bud pollination using hand labor. Such large scale increase of inbred lines is most commonly done in a greenhouse or plastic house. This practice of parent line seed production leads to good quality seed and disease control. Inbred broccoli plants according to the invention include for example broccoli plants of lines 550478, 550479, 550385, 550475, 550198, and 560465, and seeds or derivatives thereof. These lines can by increased by bud pollination or converted into a CMS cytoplasm. These methods are well known to a person skilled in the art.

The commercial hybrid seed is produced in the open field by inter-planting rows of the seed (female) parent and the pollinator (male) parent, where self-incompatibility or CMS of the seed parent prevents self pollination and ensures the harvesting of hybrid F1 seed, in methods well know in the art. The method for producing hybrid seed according to the invention thus involves in one embodiment the growing of rows of male and female parents having the novel growth type and the harvesting of the hybrid seeds from the female parent rows.

For broccoli hybrid seed production, the modern system uses CMS that was introgressed into *Brassica oleracea* L. from radish. Studies on the new male sterility in Japanese radish, with special reference to the utilization of this sterility towards practical raising of hybrid seed.

Thus, also provided are inbred broccoli plants according to the invention which are male sterile and are suitable for being used as a female parent in hybrid seed production. In one embodiment the inbred broccoli plants are male sterile due to cytoplasmic male sterility, e.g. the Ogura CMS. Such plants can be made as known in the art. In another embodiment the plant according to the invention is genetically male sterile or male sterile due to one or more transgenes conferring male sterility being integrated into their genome, as for example described in EP 0 344 029; U.S. Pat. No. 6,509,516; U.S. Pat. No. 5,254,802; or in U.S. Pat. No. 5,789,566, the contents of all of which are incorporated in their entirety by reference Seed from various lines of inbred broccoli with the detached floret growth type have been deposited with ATCC, as described below. This invention encompasses, plants and plant parts produced by growing such seeds, including pollen and an ovule from such plants.

EXAMPLES

Example 1

Development of Plant with Curds Having Detached Florets

Both proprietary and public research lines were available having an exserted curd or raised head (RH) trait. For instance, the Oregon State University (OSU) broccoli breeding program had lines with a moderate exserted head, and several accessions were obtained in the 1980's from the OSU breeding program. Some of these lines were designated as OSU-102 and OSU-111. These accessions produced poor head size, poor head quality, generally, and leaves on the stem just below the head which rendered such lines unsuitable as parents for commercially viable hybrids. Selection for better raised head (referred to as 'RH') traits and higher internode lengths consistently led to lower head weights. Eventually after multiple rounds of breeding and selection, lines were developed with the RH trait, and compact heavy heads of good quality.

Proprietary accessions selected at the start of the breeding project were designated DH MRE-7, DH MRD1-1, GM-1.6, B19, DH E-47, EC-2, DH GV-37, SH-2, OSU-102, OSU-111, MRD-2, HC-1, BRM56-3905, BRM53-3921, DC3EC6, 1032-1104 and 2151xT&A. All of these lines were elite parent lines developed in the Seminis breeding program, that were used for the production of commercial hybrids as long ago as the 1970s. These lines were chosen at least partly to compensate for the defects observed of the horticultural characteristics of the OSU lines.

More specifically, the proprietary lines had very good general combining ability, resistance to disease, particularly to downy mildew (*Peronospora parasitica*), already showed reasonably good RH traits, good head height and head-height uniformity, as well as resistance to bacterial soft rot (*Erwinia* and *Pseudomonas* bacteria). The pedigree for lines 550478, 550198, 550479 and 550385 are provided in FIG. 1. The pedigree for line 550475 is provided in FIG. 2 and for line 560465 is provided in FIG. 3.

The designation DH designates double haploid, and indicates that these lines have been developed through microspore culture, followed by chromosome doubling.

All genetic materials or lines have been developed after many years of crossing and selection. Details of this crossing and selection program are described in FIGS. 1, 2 and 3. Progeny plants (F1) of each cross were selected for their phenotypic appearance for head exsertion in combination with favorable horticultural characteristics for all other important horticultural and head traits. The selected plants from the best families were crossed again with other selected plants from other families. Occasionally, between two crossing cycles selected plants were selfed for one or two generations (F2, F3) to obtain better uniformity of the lines.

The best plants of these lines were crossed again. This breeding procedure is known as the modified family selection, as is described in standard text books of plant breeding, e.g., Allard, R. W., *Principles of Plant Breeding* (1960) New York, N.Y., Wiley, pp 485; Simmonds, N. W., *Principles of Crop Improvement* (1979), London, UK, Longman, pp 408; Sneep, J. et al., (1979) *Plant breeding perspectives*, PUDOC Wageningen, The Netherlands; Mark J. Basset, (ed), *Breeding of Vegetable Crops*, (1986) AVI Publ. Comp. Westport, U.S.A.; Fehr, W. R. et al., *Principles of Cultivar Development—Theory and Technique* (1987) MacMillan, New York, N.Y.

In the course of the selection program several lines showing favorable characteristics were selected which were designated as PLH, and associated with a sequence number.

Crossing of lines with curds showing semi-detached florets (BRM56-3905/BRM53-5913) with lines having fully exserted heads (PLH2546/PLH33) led to the development of line 520166 (PLH2546/PLH33/BRM56-3905/BRM53-3913). The pedigree is provided in FIG. 1.

Figure 2:
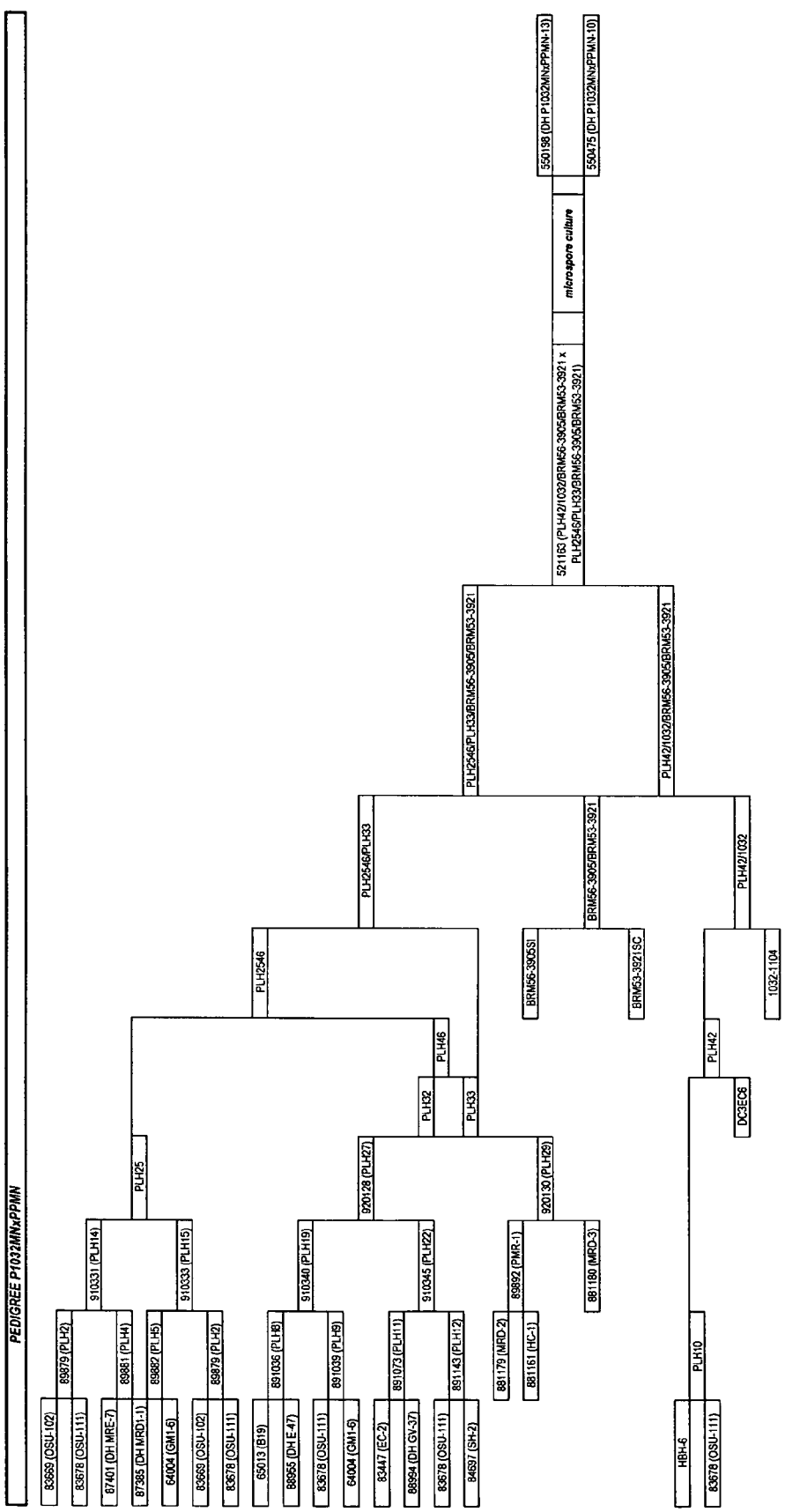
FIG. 2 is a chart showing the pedigree of the development of the detached floret lines 550475 and 550198.
Figure 3:
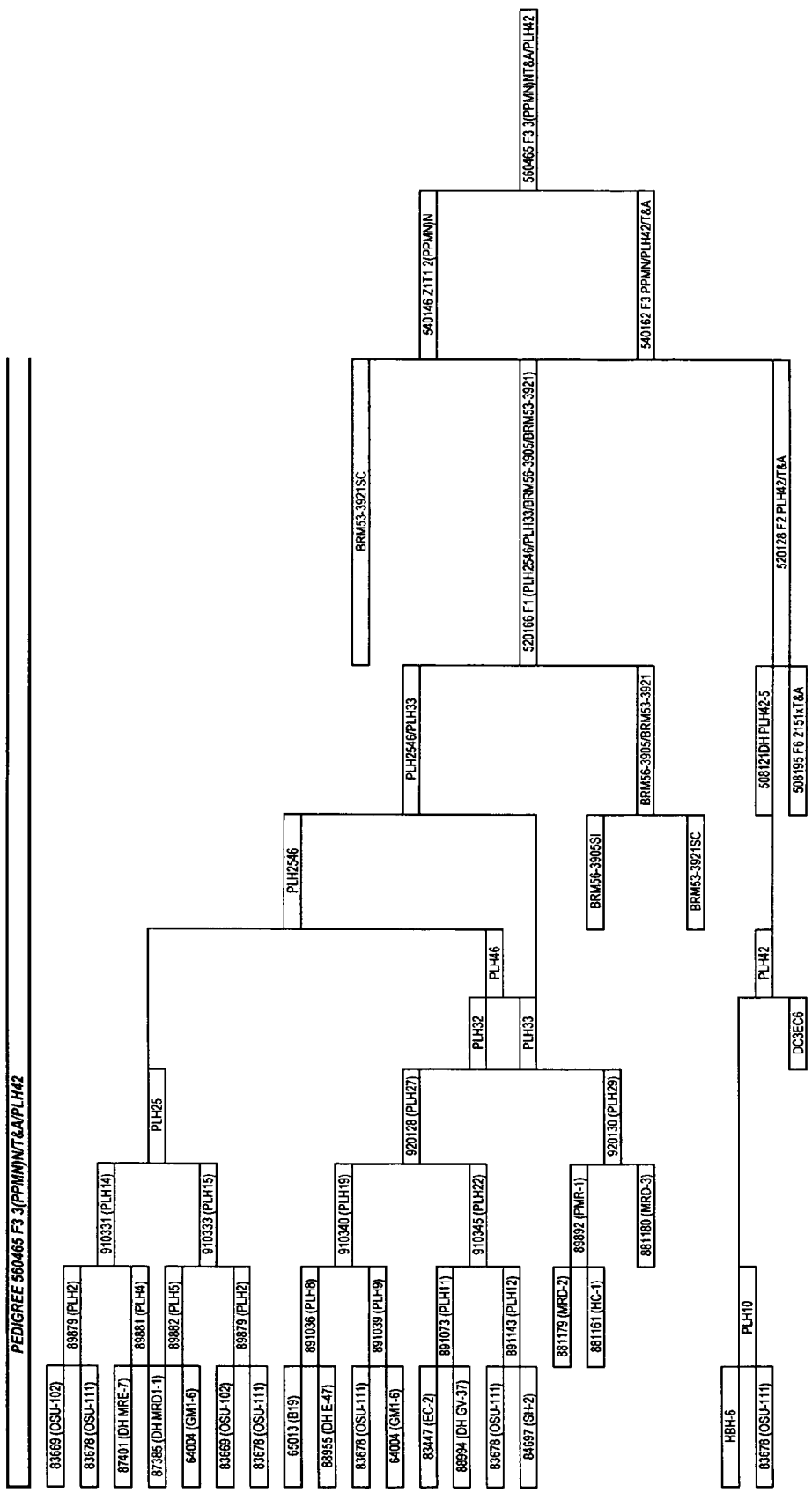
FIG. 3 is a chart showing the pedigree of the development of the detached floret line 560465.

FIG. 2 shows the pedigree for line 521163. Line 521163, originated from a cross between line PLH42/1032/BRM56-3905/BRM53-3913 (semi-detached) and PLH2546/plh33/brm56-3905.brm53-3913 with fully exserted head. This led to the selection of a line designated 521163, which similarly to line 520166 shows branched curds with detached florets.

Example 2

Microspore Culture

Lines 520166 and 521163 were used as the starting material for the microspore culture. Anthers from heterozygous donor plants grown under a 16 h photoperiod at 10-12° C. are used as experimental material. Flower buds of different sizes are harvested and isolated, anthers were squashed and stained with DAPI to determine the stage of meiotic development. Flower buds containing anthers with pollen in late uni-nucleate to early bi-nucleate stage are selected and sterilized by spraying with 96% ethanol, followed by immersion in a 2.6% solution of sodium hypochlorite for 5 min and rinsed three times with sterilized distilled water.

The sterilized buds are prepared in B5 liquid medium and buds are squashed as described in Fan, Z., Armstrong, K. C. and Keller, W. A., *Development of microspores in vivo and in vitro in Brassica napus* L., *Protoplasma* 147, 191-199 (1988). The resulting squashed buds are then filtered through two nylon filters (48 μm, 63 μm Ø) and centrifuged (100 g, 8° C., 4 min), and the pellet is washed 3 times in 27 ml B5 liquid medium. A small amount of charcoal is added and the pellet re-suspended in a liquid culture medium as described in Lichter, R. Z., *Anther culture of Brassica napus in a liquid culture medium, Planzenphysiol.* 103, 229-237 (1981) and in Lichter R. Z., *Induction of haploid plants from isolated pollen of Brassica napus, Planzenphysiol.* 105, 427-437 (1982) with a final density of 1 flower bud per ml of this medium. The microspore suspension cultures are incubated in the dark at 35° C. for 24 h and then grown in the dark at 25° C.

After 3 to 6 weeks embryos appear and are transferred to a plant regeneration medium, as described by in Keller, W. A. and Armstrong, K. C., *Embryogenesis and plant regeneration in Brassica napus anther cultures, Can. J. Bot.* 55, 1383-1388 (1977) incubated in continuous light at 8° C. for 1 week. Subsequently, the embryos were transferred to conditions of 16 h photoperiod of indirect light at 25° C. After 4 weeks plant-like structures with meristems were transferred to a rooting medium (4.44 g/l MS basic salts including vitamins without myo-inositol (purchased from Duchefa as MS Royal Sluis), 100 mg/l myo-inositol (purchased from BDH), 400 μg/l Thiamine HCl (Duchefa), 200 μg/l IBA (Duchefa), 30 g/l sucrose (Duchefa), 10 g/l plant agar (Duchefa), pH adjusted to 5.8) and grown under a 16 h photoperiod at 20° C. Regenerated plantlets are transferred on fresh rooting medium once every 4 weeks.

This procedure is continued until plants are delivered to the breeder for further selection and breeding. Plants of unknown ploidy level are provided to the breeder. The breeder selects those plants that are phenotypically desirable, fertile and produce identical fully homozygous progeny.

Inbred lines are tested and those that give the best hybrid performance are identified and selected. Hybrid seed can be produced indefinitely, as long as the homogeneity and the homozygosity of the inbred parents is maintained.

Heterozygous lines 520166 (PLH2546/PLH33/BRM56-3905/BRM53-3913) and 521163 ((PLH42/1032/BRM56-3905/BRM53-3913×PLH2546/PLH33/BRM56-3905/BRM53-3913) were used as the starting material for the microspore experiment. Broccoli lines 550478, 550479, 550198, and 550385 were obtained from the microspore culture of 520166. Broccoli line 550475 was obtained from microspore culture of 521163. These lines were selected on the basis of the detached and uniformly green florets combined with desirable horticultural traits.

Seed samples obtained from representative broccoli lines having detached florets were deposited under NCIMB accession numbers as follows: Seeds of broccoli line 550479 were deposited under NCIMB Accession No. 41415; seeds of broccoli line 550478 were deposited under NCIMB Accession No. 41416; and seeds of broccoli line 550385 were deposited under NCIMB Accession No. 41417. Seeds of broccoli line 550198 were deposited under NCIMB Accession No. 41418.

Example 3

Additional Inbred Broccoli Lines

Additional inbred broccoli lines are developed from crosses using broccoli line 520166, described above. The pedigree of broccoli line 560465 is provided in FIG. 3.

Figure 4:
FIG. 4 provides a photograph of severed florets from broccoli type RS1149.
Figure 5:
FIG. 5 provides a photograph of a head of an embodiment of a broccoli line of the present invention.
Figure 6:
FIG. 6 provides a photograph of severed florets from one embodiment of a broccoli line of the present invention.

Measurements are taken from a commercial crown broccoli hybrid (RS1149, or Tinman), a crown broccoli hybrid line, 550118, and the two detached floret lines, 560465 and 550475. FIG. 4 provides a photograph of several outer florets of commercial broccoli hybrid RS1149, and FIGS. 5 and 6 provide photographs of an intact head, and several severed florets, respectively, of broccoli line 550465. The following data are collected from the broccoli plants and are provided in Table 1 below. The minimum distance of each floret to the nearest floret in the curd (in millimeters); the widest diameter of the floret (in millimeters); the total length of the floret from the crown to the attachment of the floret to the primary stem (in millimeters); the quality rating of each floret (on a scale of 1 to 5; 1 being very poor, 2 being poor, 3 being medium, 4 being good, and 5 being very good); the color of the top of the floret (using the color chart from the Royal Horticultural Society); the color of the shoulder of the floret (also using the color chart from the RHS); the percent yellow of the floret (percent shoulder of the total floret); the color of the stem of the floret (based on the RHS color chart); and the weight of the square floret (the length of the floret cut to the same size as the diameter of the floret).

TABLE 1

| FIELD # | MNR | PLANT # | FLORET# | MIN. DISTANCE TO NEAREST FLORET (mm) | DIAMETER (mm) | TOTAL LENGTH (mm) | QUALITY RATING (1–5) | FLORET COLOR TOP | FLORET COLOR SHOULDER | % SHOULDER/ TOTAL | FLORET COLOR STEM | WEIGHT SQUARE FLORET (gr) |
|---|---|---|---|---|---|---|---|---|---|---|---|---|
| 232 | RS1149 | 1 | 1 | 3 | 40 | 70 | 4 | N138B | 154C | X | 145A | 7 |
|  |  |  | 2 | 0 | 65 | 75 | 4 | N138B | 154C | X | 145A | 24 |
|  |  |  | 3 | 0 | 60 | 60 | 3 | N138B | 154C | X | 145B | 18 |
|  |  |  | 4 | 0 | 75 | 65 | 4 | N138B | 154C | X | 145B | 37 |

TABLE 1-continued

| FIELD # | MNR | PLANT # | FLO-RET# | MIN. DISTANCE TO NEAREST FLORET (mm) | DIAMETER (mm) | TOTAL LENGTH (mm) | QUALITY RATING (1–5) | FLORET COLOR TOP | FLORET COLOR SHOULDER | % SHOULDER/ TOTAL | FLORET COLOR STEM | WEIGHT SQUARE FLORET (gr) |
|---|---|---|---|---|---|---|---|---|---|---|---|---|
| | | | 5 | 0 | 70 | 60 | 4 | N138B | 154C | X | 145C | 32 |
| | | | 6 | 0 | 80 | 55 | 4 | N138B | 154C | X | 145C | 33 |
| | | | 7 | 0 | 65 | 55 | 3.5 | N138B | 154C | X | 145D | 23 |
| | | | 8 | 0 | 60 | 50 | 4 | N138B | 154C | X | 145D | 26 |
| | | | 9 | 0 | 40 | 45 | 4 | N138B | 154C | X | 145D | 12 |
| | | | 10 | 0 | 40 | 40 | 3 | N138B | 154C | X | 145D | 9 |
| 1037 | 550118 | 1 | 1 | 0 | 50 | 60 | 3 | N138B | 154C | 25 | 145B | 14 |
| | | | 2 | 0 | 60 | 50 | 4 | N138B | 154C | 20 | 145B | 16 |
| | | | 3 | 0 | 60 | 45 | 4 | N138B | 154D | 25 | 145B | 18 |
| | | | 4 | 0 | 70 | 55 | 4 | N138B | 154D | 15 | 145B | 29 |
| | | | 5 | 0 | 60 | 50 | 4 | N138B | 154D | 15 | 145B | 22 |
| | | | 6 | 0 | 60 | 50 | 4 | N138B | 154C | 10 | 145B | 21 |
| | | | 7 | 0 | 50 | 45 | 4 | N138B | 154D | 15 | 145C | 14 |
| | | | 8 | 0 | 50 | 40 | 3.5 | N138B | 154D | 15 | 145C | 13 |
| | | | 9 | 0 | 45 | 40 | 3 | N138B | 154D | 20 | 145D | 9 |
| | | | 10 | 0 | 40 | 40 | 3 | N138B | 154D | 15 | 145D | 8 |
| | | 2 | 1 | 0 | 60 | 60 | 4 | N138B | 154B | 15 | 145B | 21 |
| | | | 2 | 0 | 60 | 50 | 4 | N138B | 154C | 15 | 145B | 21 |
| | | | 3 | 0 | 55 | 50 | 4 | N138B | 154B | 15 | 145B | 14 |
| | | | 4 | 0 | 65 | 50 | 4 | N138B | 154D | 15 | 145C | 19 |
| | | | 5 | 0 | 65 | 50 | 4 | N138B | 154D | 10 | 145C | 25 |
| | | | 6 | 0 | 50 | 45 | 4 | N138B | 154D | 10 | 145D | 13 |
| | | | 7 | 0 | 55 | 45 | 3 | N138B | 154D | 10 | 145D | 15 |
| | | | 8 | 0 | 50 | 40 | 3.5 | N138B | 154D | 10 | 145D | 12 |
| | | | 9 | 0 | 45 | 35 | 3 | N138B | 154D | 20 | 145D | 9 |
| | | | 10 | 0 | 40 | 35 | 3 | N138B | 154D | 15 | 145D | 8 |
| 1037 | | AV | | 0 | 54.5 | 46.75 | 3.65 | N138B | 154B–D | 15.5 | 145B–D | 16.05 |
| 1300 | 560465 | 1 | 1 | 10 | 50 | 220 | 4 | N138C | NA | NA | N138C | 17 |
| | | | 2 | 12 | 60 | 200 | 4 | N138C | NA | NA | N138C | 20 |
| | | | 3 | 1 | 55 | 180 | 4 | N138C | NA | NA | N138C | 18 |
| | | | 4 | 30 | 60 | 210 | 4 | N138C | NA | NA | N138C | 17 |
| | | | 5 | 3 | 60 | 180 | 3 | N138C | NA | NA | N138C | 15 |
| | | | 6 | 3 | 45 | 120 | 3 | N138C | NA | NA | N138C | 18 |
| | | | 7 | 10 | 50 | 140 | 4 | N138C | NA | NA | N138C | 12 |
| | | | 8 | 3 | 50 | 125 | 3 | N138C | NA | NA | N138C | 9 |
| | | | 9 | 0 | 40 | 100 | 2 | N138C | NA | NA | N138C | 6 |
| | | | 10 | 0 | 25 | 80 | 2 | N138C | NA | NA | N138C | 3 |
| | | 2 | 1 | 1 | 35 | 260 | 4 | N138C | NA | NA | N138C | 6 |
| | | | 2 | 20 | 55 | 200 | 4 | N138C | NA | NA | N138C | 17 |
| | | | 3 | 10 | 50 | 170 | 4 | N138C | NA | NA | N138C | 13 |
| | | | 4 | 14 | 50 | 155 | 4 | N138C | NA | NA | N138C | 11 |
| | | | 5 | 15 | 60 | 125 | 4 | N138C | NA | NA | N138C | 12 |
| | | | 6 | 20 | 45 | 120 | 4 | N138C | NA | NA | N138C | 9 |
| | | | 7 | 14 | 35 | 100 | 4 | N138C | NA | NA | N138C | 6 |
| | | | 8 | 1 | 35 | 75 | 3 | N138C | NA | NA | N138C | 3 |
| 1300 | | AV | | 8.35 | 43 | 138 | 3.2 | N138C | NA | NA | N138C | 11.563 |
| 1305 | 550475 | 1 | 1 | 10 | 40 | 230 | 2 | 139C | NA | NA | 139D | 6 |
| | | | 2 | 20 | 75 | 170 | 4 | 139C | NA | NA | 139D | 25 |
| | | | 3 | 2 | 50 | 150 | 3 | 139C | NA | NA | 139D | 9 |
| | | | 4 | 5 | 40 | 115 | 4 | 139C | NA | NA | 139D | 7 |
| | | | 5 | 4 | 55 | 145 | 4 | 139C | NA | NA | 139D | 20 |
| | | | 6 | 5 | 50 | 160 | 3.5 | 139C | NA | NA | 139D | 14 |
| | | | 7 | 5 | 45 | 145 | 3 | 139C | NA | NA | 139D | 7 |
| | | | 8 | 5 | 55 | 110 | 4 | 139C | NA | NA | 139D | 13 |
| | | | 9 | 2 | 45 | 115 | 3.5 | 139C | NA | NA | 139D | 8 |
| | | | 10 | 1 | 40 | 90 | 3.5 | 139C | NA | NA | 139D | 6 |
| | | 2 | 1 | 3 | 45 | 280 | 3 | 139C | NA | NA | 139D | 8 |
| | | | 2 | 13 | 40 | 245 | 2 | 139C | NA | NA | 139D | 7 |
| | | | 3 | 5 | 55 | 215 | 3 | 139C | NA | NA | 139D | 15 |
| | | | 4 | 15 | 55 | 180 | 3 | 139C | NA | NA | 139D | 13 |
| | | | 5 | 11 | 60 | 190 | 4 | 139C | NA | NA | 139D | 20 |
| | | | 6 | 16 | 60 | 175 | 2 | 139C | NA | NA | 139D | 4 |
| | | | 7 | 1 | 30 | 115 | 4 | 139C | NA | NA | 139D | 16 |
| | | | 8 | 6 | 45 | 125 | 4 | 139C | NA | NA | 139D | 9 |
| | | | 9 | 1 | 40 | 111 | 4 | 139C | NA | NA | 139D | 8 |
| | | | 10 | 3 | 35 | 85 | 3 | 139C | NA | NA | 139D | 3 |
| 1305 | | AV | | 6.65 | 48 | 157.6 | 3.325 | 139C | NA | NA | 139D | 10.9 |

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A broccoli seed capable of producing a broccoli plant comprising a main curd having florets, wherein at least 50% of said florets on said main curd do not touch another floret on said main curd, and said broccoli plant is a cultivar of Brassica oleracea var. italica, and said broccoli plant shares a genetic source with a broccoli line selected from the group consisting of line 550478, having seed deposited under NCIMB Accession No. 41416; line 550479, having seed deposited under NCIMB Accession No. 41415; line 550385, having seed deposited under NCIMB Accession No. 41417; and line 550198, having seed deposited under NCIMB Accession No. 41418; and said genetic source provides a main curd having at least 50% of florets that do not touch another floret on said main curd.

2. The broccoli seed of claim 1, wherein at least 60% of said florets do not touch another floret on said curd.

3. The broccoli seed of claim 2, wherein at least 70% of said florets do not touch another floret on said curd.

4. The broccoli seed of claim 3, wherein at least 80% of said florets do not touch another floret on said curd.

5. The broccoli seed of claim 4, wherein at least 90% of said florets do not touch another floret on said curd.

6. The broccoli seed of claim 1, wherein said florets have substantially no yellowing.

7. The broccoli seed of claim 6, wherein said florets have an absence of yellowing.

8. The broccoli seed of claim 1, wherein said curd comprises at least six florets.

9. The broccoli seed of claim 8, wherein said curd comprises at least 20 florets.

10. The broccoli seed of claim 9, wherein said curd comprises at least 30 florets.

11. A container comprising broccoli seeds capable of producing broccoli plants comprising a main curd having florets, wherein said broccoli plants grown from greater than 50% of said seeds have greater than 50% of said florets that do not touch another floret on the said main curd, and said broccoli plant is a cultivar of Brassica oleracea var. italica, and said broccoli plant shares a genetic source with a broccoli line selected from the group consisting of line 550478, having seed deposited under NCIMB Accession No. 41416; line 550479, having seed deposited under NCIMB Accession No. 41415; line 550385, having seed deposited under NCIMB Accession No. 41417; and line 550198, having seed deposited under NCIMB Accession No. 41418; and
said genetic source provides a main curd having at least 50% of florets that do not touch another floret on said main curd.

12. The container of claim 11, wherein greater than 70% of said florets on said curd do not touch another floret on the same curd.

13. The container of claim 11, wherein greater than 80% of said florets on said curd do not touch another floret on the same curd.

14. The container of claim 11, wherein greater than 90% of said florets on said curd do not touch another floret on the same curd.

15. The container of claim 11, wherein said curd comprises at least 12 florets.

16. The container of claim 11, wherein said curd comprises at least 20 florets.

17. The container of claim 11, wherein said curd comprises at least 30 florets.

18. The container of claim 11, wherein said florets not touching another floret on the same curd have substantially no yellowing.

19. The container of claim 18, wherein said florets not touching another floret on the same curd florets have an absence of yellowing.

20. A part of a broccoli plant comprising a main curd having florets wherein at least 50% of said florets on said main curd do not touch another floret within the-same said main curd, wherein said broccoli plant is a cultivar of *Brassica oleracea var. italica*, and said broccoli plant shares a genetic source with a broccoli line selected from the group consisting of line 550478, having seed deposited under NCIMB Accession No. 41416; line 550479, having seed deposited under NCIMB Accession No. 41415; line 550385, having seed deposited under NCIMB Accession No. 41417; and line 550198, having seed deposited under NCIMB Accession No. 41418; and
said genetic source provides a main curd having at least 50% of florets that do not touch another floret on said main curd.

21. A seed, endosperm, ovule, or pollen of a broccoli plant, wherein said broccoli plant comprises florets, wherein at least 50% of said florets on the main curd do not touch another floret within the-same said main curd, and said broccoli plant is a cultivar of *Brassica oleracea var. italica*, and said broccoli plant shares a genetic source with a broccoli line selected from the group consisting of line 550478, having seed deposited under NCIMB Accession No. 41416; line 550479, having seed deposited under NCIMB Accession No. 41415; line 550385, having seed deposited under NCIMB Accession No. 41417; and line 550198, having seed deposited under NCIMB Accession No. 41418; and said genetic source provides a main curd having at least 50% of florets that do not touch another floret on said main curd.

22. A broccoli plant grown from the seed of claim 1.

23. The broccoli seed of claim 6, wherein said florets have less than about 5% yellowing as measured by the percentage of coverage across the floret having a more yellow than green appearance measured as an average yellowing of a population of florets from a curd at maturity of the floret at harvest.

24. The broccoli seed of claim 23, wherein said florets are less than about 5% yellow-green.

25. The broccoli seed of claim 24, wherein said yellow-green florets have a color score in of 144B/C, 145B/C/D, 149D-150D, and 154B/C/D on the Royal Horticultural Society (RHS) Color Chart.

26. The broccoli seed of claim 1, wherein said florets have an average weight of about 10 grams.

27. The broccoli seed of claim 1, wherein said florets not touching another floret on said curd have a color score in the RHS color chart selected from the group consisting of 137A, 137B, 138A, 138B, 138C, and 139D.

28. The part of a broccoli plant of claim 20, wherein said florets are less than about 5% yellow-green.

29. The part of a broccoli plant of claim 28, wherein said yellow-green florets have a color score in of 144B/C, 145B/C/D, 149D-150D, and 154B/C/D on the Royal Horticultural Society (RHS) Color Chart.

30. The part of a broccoli plant of claim 29, wherein said florets are between 4 and 10 centimeters in diameter.

31. The part of a broccoli plant of claim 20, wherein said curd comprises at least 16 florets.

32. The part of a broccoli plant of claim 31, wherein at least one of said florets has a length of at least eight centimeters.

33. The part of a broccoli plant of claim 20, further comprising a stalk of said floret having a length of at least seven centimeters.

34. The broccoli seed of claim 1, wherein said broccoli plant has a curd comprising at least about seven millimeters between florets.

35. The broccoli seed of claim 5, wherein said broccoli plant has a curd comprising at least 95% of florets on each curd that do not touch another floret on the same curd.

36. The seed of claim 21, capable of growing into a broccoli plant with at least 50% of florets on any curd that do not touch another floret within the same curd.

37. An $F_1$ broccoli plant obtainable by crossing a first broccoli plant with a second broccoli plant, wherein said first broccoli plant comprises a main curd having florets, wherein at least 50% of said florets on said main curd do not touch another floret on said main curd, and said $F_1$ broccoli plant comprises a main curd having florets, wherein at least 50% of said florets on said main curd do not touch another floret on said main curd, and said first broccoli plant is a cultivar of *Brassica oleracea var. italica*, and said first broccoli plant shares a genetic source with a broccoli line selected from the group consisting of line 550478, having seed deposited under NCIMB Accession No. 41416; line 550479, having seed deposited under NCIMB Accession No. 41415; line 550385, having seed deposited under NCIMB Accession No. 41417; and line 550198, having seed deposited under NCIMB Accession No. 41418; and said genetic source provides a main curd having at least 50% of florets that do not touch another floret on said main curd.

38. The $F_1$ broccoli plant of claim 37, wherein said first broccoli plant is from a broccoli line selected from the group consisting of line 550478, having seed deposited under NCIMB Accession No. 41416; line 550479, having seed deposited under NCIMB Accession No. 41415; line 550385, having seed deposited under NCIMB Accession No. 41417; and line 550198, having seed deposited under NCIMB Accession No. 41418.

39. The broccoli seed of claim 1, wherein said curd is exserted above the leaf canopy.

40. The broccoli seed of claim 1, wherein the crown of said curd is raised by at least 2 centimeters above the leaf canopy of said broccoli plant.

41. The container of claim 11, wherein said container comprises at least about 10, at least about 100, at least about 1000, at least about 2500, or at least about 5000 seeds.

42. The container of claim 11, wherein said container comprises at least about 1 ounce, at least about 1 pound, at least about 3 pounds, or at least about 5 pounds seeds.

43. The broccoli seed of claim 1, wherein said seed is obtainable from a progeny broccoli plant of a broccoli line selected from the group consisting of line 550478, having seed deposited under NCIMB Accession No. 41416; line 550479, having seed deposited under NCIMB Accession No. 41415; line 550385, having seed deposited under NCIMB Accession No. 41417; and line 550198, having seed deposited under NCIMB Accession No. 41418.

44. The broccoli seed of claim 1, wherein said seed is derived from a broccoli line selected from the group consisting of line 550478, having seed deposited under NCIMB Accession No. 41416; line 550479, having seed deposited under NCIMB Accession No 41415; line 550385, having seed deposited under NCIMB Accession No. 41417; and line 550198, having seed deposited under NCIMB Accession No. 41418.

45. The broccoli seed of claim 1, wherein said seed is obtained from a plant whose pedigree traces back to a broccoli plant of a broccoli line selected from the group consisting of line 550478, having seed deposited under NCIMB Accession No. 41416; line 550479, having seed deposited under NCIMB Accession No. 41415; line 550385, having seed deposited under NCIMB Accession No. 41417; and line 550198, having seed deposited under NCIMB Accession No. 41418.

46. The broccoli seed of claim 1, wherein said seed is produced from a progeny broccoli plant of a broccoli line selected from the group consisting of line 550478, having seed deposited under NCIMB Accession No. 41416; line 550479, having seed deposited under NCIMB Accession No. 41415; line 550385, having seed deposited under NCIMB Accession No. 41417; and line 550198, having seed deposited under NCIMB Accession No. 41418.

47. The container of claim 11, wherein said seed is obtainable from a progeny broccoli plant of a broccoli line selected from the group consisting of line 550478, having seed deposited under NCIMB Accession No. 41416; line 550479, having seed deposited under NCIMB Accession No. 41415; line 550385, having seed deposited under NCIMB Accession No. 41417; and line 550198, having seed deposited under NCIMB Accession No. 41418.

48. The container of claim 11, wherein said seed is derived from a broccoli line selected from the group consisting of line 550478, having seed deposited under NCIMB Accession No. 41416; line 550479, having seed deposited under NCIMB Accession No. 41415; line 550385, having seed deposited under NCIMB Accession No. 41417; and line 550198, having seed deposited under NCIMB Accession No. 41418.

49. The container of claim 11, wherein said seed is obtained from a plant whose pedigree traces back to a broccoli plant of a broccoli line selected from the group consisting of line 550478, having seed deposited under NCIMB Accession No. 41416; line 550479, having seed deposited under NCIMB Accession No. 41415; line 550385, having seed deposited under NCIMB Accession No. 41417; and line 550198, having seed deposited under NCIMB Accession No. 41418.

50. The container of claim 11, wherein said seed is produced from a progeny broccoli plant of a broccoli line selected from the group consisting of line 550478, having seed deposited under NCIMB Accession No. 41416; line 550479, having seed deposited under NCIMB Accession No. 41415; line 550385, having seed deposited under NCIMB Accession No. 41417; and line 550198, having seed deposited under NCIMB Accession No. 41418.

51. A broccoli seed, wherein said seed is from a broccoli line selected from the group consisting of line 550478, having seed deposited under NCIMB Accession No. 41416; line 550479, having seed deposited under NCIMB Accession No. 41415; line 550385, having seed deposited under NCIMB Accession No. 41417; and line 550198, having seed deposited under NCIMB Accession No. 41418.

* * * * *

UNITED STATES PATENT AND TRADEMARK OFFICE
CERTIFICATE OF CORRECTION

| | | |
|---|---|---|
| PATENT NO. | : 8,026,416 B2 | |
| APPLICATION NO. | : 11/602276 | |
| DATED | : September 27, 2011 | |
| INVENTOR(S) | : Franciscus van den Bosch et al. | |

It is certified that error appears in the above-identified patent and that said Letters Patent is hereby corrected as shown below:

Title Page:

Item (73), Assignee, please change "Vegatable" to --Vegetable--.

Column 21, lines 12 and 13, please change "Brassica oleracea var. italica" to --*Brassica oleracea* var. *italica*--;

line 24, please change "said curd" to --said main curd--;
    line 26, please change "said curd" to --said main curd--;
    line 28, please change "said curd" to --said main curd--;
    line 30, please change "said curd" to --said main curd--;
    line 35, please change "said curd" to --said main curd--;
    line 37, please change "said curd" to --said main curd--;
    line 39, please change "said curd" to --said main curd--;
    line 45, please change "the said main" to --said main--;
    line 46, please change "*oleracea var. italica*" to --*oleracea* var. *italica*--;
    line 58, please change "said curd" to --said main curd--;
    lines 58 and 59, please change "the same curd" to --said main curd--;
    line 61, please change "said curd" to --said main curd--;
    lines 61 and 62, please change "the same curd" to --said main curd--;

Column 21, line 64, please change "said curd" to --said main curd--;
    lines 64 and 65, please change "the same curd" to --said main curd--; and
    line 66, please change "said curd" to --said main curd--.

Signed and Sealed this
Thirteenth Day of December, 2011

David J. Kappos
*Director of the United States Patent and Trademark Office*

CERTIFICATE OF CORRECTION (continued)
U.S. Pat. No. 8,026,416 B2

Column 22, line 1, please change "said curd" to --said main curd--;

line 3, please change "said curd" to --said main curd--;

line 6, please change "the same curd" to --said main curd--;

line 9, please change "the same curd" to --said main curd--;

line 12, please change "florets wherein" to --florets, wherein--;

line 13, please change "within the-same said" to --within said--;

line 15, please change "*oleracea var. italica*" to --*oleracea* var. *italica*--;

line 29, please change "within the-same said" to --within said--;

line 30, please change "*oleracea var. italica*" to --*oleracea* var. *italica*--;

line 45, please change "a curd" to --a main curd--;

line 49, please change "in of" to --of--;

line 55, please change "said curd" to --said main curd--;

line 61, please change "in of" to --of--; and lines 66 and 67, please change "said curd" to --said main curd--.

Column 23, line 7, please change "a curd" to --a main curd--;

lines 9 and 10, please delete "said broccoli plant has a curd comprising";

lines 10 and 11, please delete "on each curd that";

line 11, please change "the same curd" to --said main curd--;

please change "95% of florets" to --95% of said florets--;

line 13, please change "with" to --wherein--;

please change "any curd" to --any main curd--;

line 14, please change "same curd" to --same main curd--;

line 23, please change "*oleracea var. italica*" to --*oleracea* var. *italica*--;

line 41, please change "said curd" to --said main curd--;

lines 43 and 44, please change "said curd" to --said main curd--; and line 51, please change "pounds seeds" to --pounds of seeds--.